United States Patent
Holmes et al.

(10) Patent No.: US 7,173,156 B1
(45) Date of Patent: Feb. 6, 2007

(54) THIOACETATE DEPROTECTION

(75) Inventors: Brian T Holmes, Arlington, VA (US); Arthur W Snow, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/279,153

(22) Filed: Apr. 10, 2006

Related U.S. Application Data

(60) Provisional application No. 60/734,254, filed on Nov. 2, 2005.

(51) Int. Cl.
*C07C 319/02* (2006.01)

(52) U.S. Cl. .............................. 568/61; 568/65; 568/66; 568/67; 568/69; 560/231

(58) Field of Classification Search ................. 560/231; 568/61, 65, 66, 67, 69

See application file for complete search history.

(56) References Cited

OTHER PUBLICATIONS

Gregory et al., "Nucleophilic Displacement Reactions at the Thiol Ester Bond. V. Reactions of 2,2,2-Trifluoroethyl Thiolacetate" *J. Am. Chem. Soc.*, 89(9), 2121-2127 (1967).

Herzig et al., "Studies in Sugar Chemistry. 2. A Simple Method for O-Deacylation of Polyacylated Sugars" *J. Org. Chem.*, 51(5), 727-730 (1986).

Hibbert et al., "Acylation. Part XXIV. The Cyanide Catalysed Hydrolysis of Esters" *J. Chem. Soc. B: Phys. Org.*, 5, 565-568 (1968).

Holmes et al., "Aliphatic thioacetate deprotection using catalytic tetrabutylammonium cyanide" *Tetrahedron*, 61, 12339-12342 (2005).

Holmes et al., "Thioacetate Deprotection Using Catalytic Tetrabutylammonium Cyanide" MRS Fall 2005 Meeting, Poster Session (Nov. 27, 2005-Dec. 2, 2005).

*Primary Examiner*—Peter O'Sullivan
(74) *Attorney, Agent, or Firm*—John J. Karasek; Joseph T. Grunkemeyer

(57) ABSTRACT

A method of thioacetate deprotection by providing a compound of the formula $R^1$—S—CO—$R^2$, and reacting the compound with a quaternary ammonium cyanide salt in the presence of a protic solvent in an inert atmosphere to convert the compound to a product of the formula $R^1$—SH. $R^1$ is an organic group in which the bonding to sulfur is through a saturated carbon, and $R^2$ is an aliphatic group.

18 Claims, 2 Drawing Sheets

THIOACETATE DEPROTECTION

This application claims the benefit of U.S. Provisional Application Ser. No. 60/734,254, filed on Nov. 2, 2005, and incorporated herein by reference.

FIELD OF THE INVENTION

The invention relates generally to chemical methods of thioacetate deprotection.

DESCRIPTION OF RELATED ART

The synthesis of thiol protected molecules and their deprotection are increasingly important prerequisites in the development of chemical self-assembly methods. Many applications are dependent on this chemistry. These include the fabrication of nano and molecular electronic structures, soft lithography, contact printing, fabrication of nanoparticulate composites, vapor and condensed phase sensors, surface immobilization of biomolecular1 and synthetic dye functionalities, corrosion resistance treatments, adhesion promotion, biomolecular surface passivation, and electrode modification.

A particularly important issue in employing the thiol group for these purposes is its shelf life prior to use. The thiol group is sensitive to slow oxidation to a disulfide or sulfoxide under ambient conditions. As such, derivatization with a protecting group provides for long term stability. Acylation to a thioacetate is the most frequently employed protective chemistry. Deprotection of this thioacetate group back to the thiol is a necessary step for practical use thiol agents. Although numerous deprotection methods for this transformation of the thioacetate to the free thiol have been developed, many involve harsh conditions and are accompanied by significant formation of unwanted side-products including disulfides. Reported conditions include strong acids or bases which can be particularly adverse to multifunctional thioacetate moieties and often result in poor yields and mixtures. Deprotecting reagents such as ammonium hydroxide, potassium hydroxide, sulfuric acid, hydrogen cyanide, hydrochloric acid, sodium thiomethoxide, potassium carbonate, and lithium aluminum hydride are employed with variable results. (Inman et al., "In Situ Deprotection and Assembly of S-Tritylalkanethiols on Gold Yields Monolayers Comparable to Those Prepared Directly from Alkanethiols" *Langmuir,* 20, 9144 (2004); Ciszek et al., "Spontaneous Assembly of Organic Thiocyanates on Gold Surfaces, Alternative Precursors for Gold Thiolate Assemblies" *J. Am. Chem. Soc.,* 126(41), 13172 (2004); Wallace et al., "Mild, Selective Deprotection of Thioacetate using Sodium Thiomethoxide" *Tetrahedron Lett.,* 39(18), 2693 (1998); Cai et al., "Chemical and Potential-Assisted Assembly of Thiolacetyl-Terminated Oligo(phenylene ethynylene)s on Gold Surfaces" *Chem. Mater.,* 14(7), 2905 (2002); Gregory et al., "Nucleophilic Displacement Reactions at the Thiol Ester Bond. V. Reactions of 2,2,2-Trifluoroethyl Thiolacetate" *J. Am. Chem. Soc.,* 89(9), 2121 (1967); Zheng et al., "A General and Mild Synthesis of Thioesters and Thiols from Halides" *Tetrahedron Lett.,* 40(4), 603 (1999); Okada et al., "Synthesis and Antibacterial Activities of Novel Dihydrooxazine and Dihydrothiazine Ring-Fused Tricyclic Quinilonecarboxylic Acids-9-fluoro-3-methylene-10-(4-methylpiperazin-1-yl)-7-oxo-2,3-dihydro-7H-pyrido[1,2,3-de][1,4]benzoxazine-6-carboxylic Acid and its 1-Thia Congener" *J. Heterocyclic Chem.,* 28, 1061 (1991); Corey et al., "Enantioselective routes to chiral benzylic thiols, sulfinic esters and sulfonic acids illustrated by the 1-phenylethyl series" *Tetrahedron Lett.,* 33(29), 4099 (1992). All referenced patent documents and publications throughout this specification are incorporated herein by reference.) These methods typically produce better results when the S-acetyl is attached to a lengthy methylene chain segment ($(CH_2)_n$; $n \leq 6$) (Witt et al., "Applications properties and synthesis of omega-functionalized n-alkanethiols and disulfides—the building blocks of self-assembled monolayers" *Current Organic Chemistry,* 8(18), 1763 (2004).

SUMMARY OF THE INVENTION

The invention comprises a method comprising: providing a compound of the formula $R^1$—S—CO—$R^2$, and reacting the compound with a quaternary ammonium cyanide salt in the presence of a protic solvent in an inert atmosphere to convert the compound to a product of the formula $R^1$—SH. $R^1$ is an organic group in which the bonding to sulfur is through a saturated carbon, and $R^2$ is an aliphatic group.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

The disclosed method involves the use of a quaternary ammonium cyanide salt such as, but not limited to, tetrabutylammonium cyanide salt (TBACN) to catalyze the transformation of a thioester or thioacetate functional group to a free thiol at room temperature. The salt may be beneficial regarding solubility issues in comparison to potassium cyanide catalysis, which may result in only partial conversion to the free thiol. Thus, a tetrabutylammonium counter ion may be used in place of the potassium ion. Other suitable salts include, but are not limited to, tetraalkylammonium cyanide and tetra($C_1$-$C_4$)ammonium cyanide. It is reasonable to believe that the catalytic thioacetate deprotection pathway, shown below, is similar in mechanism to the solvolytic O-deacylation.

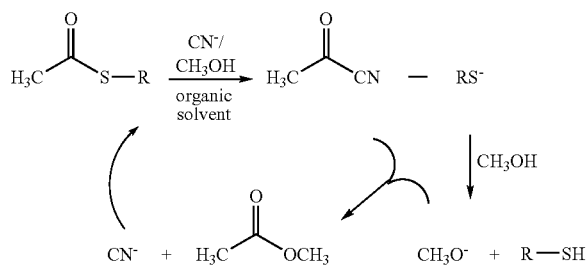

Figure 1:
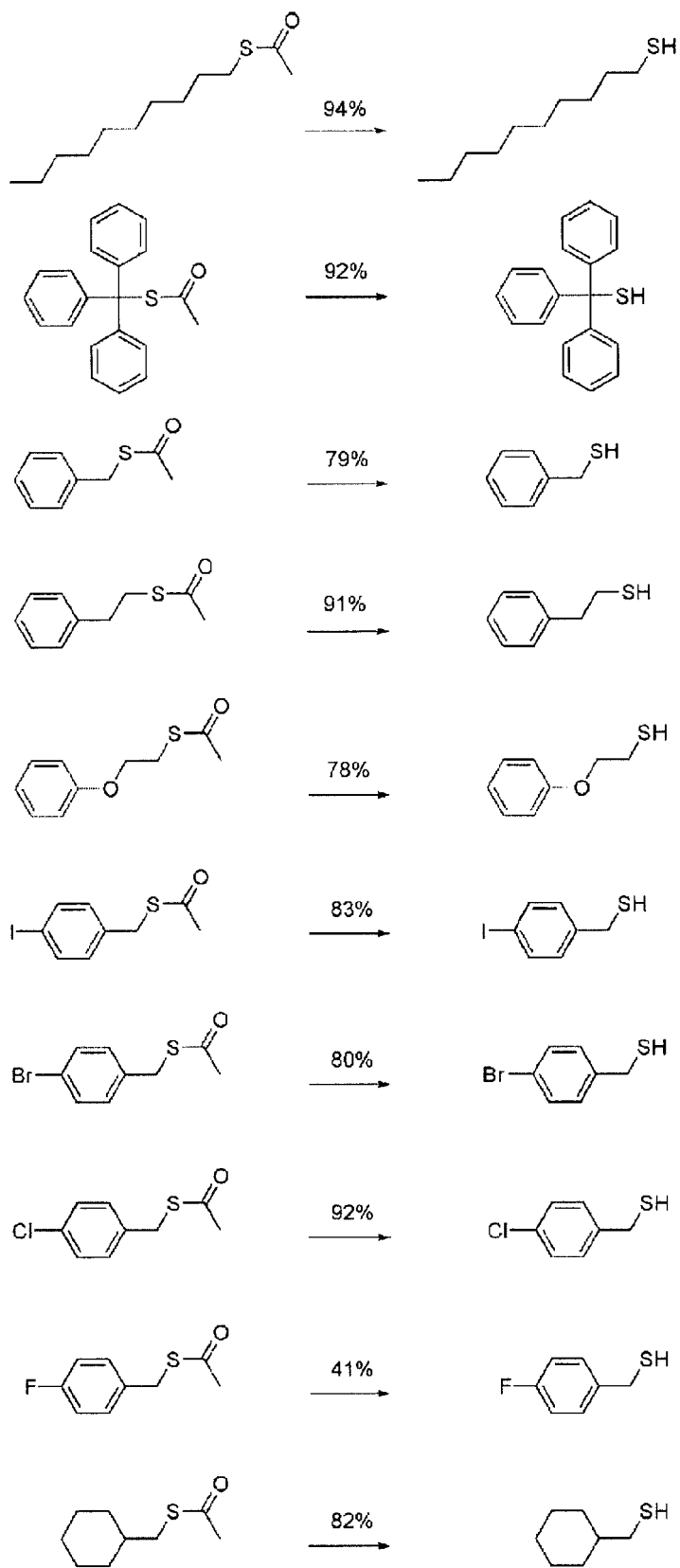
FIG. 1 shows catalytic deprotection yields of a series of available or readily synthesized aliphatic thioacetates.

Deacylation may be accomplished, for example, upon stirring for about 3 hours a solution of an aliphatic thioacetate in methanol and a cosolvent in the presence of a catalytic amount (about 0.5 molar equivalents per thioacetate) of TBACN. The reaction may proceed in high yields (>80%) at room temperature and under an oxygen-free atmosphere. (See FIG. 1. Reactions were performed in a 1:1 chloroform/MeOH solvent mixture under nitrogen using 0.5 eq. of TBACN for 3 hours.) Catalytic residue can be removed during workup, by column chromatography or distillation. The free thiols may be obtained without significant isolation/purification difficulties commonly caused by side product formation. Reactions may incorporate chloroform or dichloromethane as a cosolvent, with chloroform possibly being preferred. The reaction may be sensitive to selection of solvent as well as the presence of oxygen. It has been observed that the use of tetrahydrofuran as a cosolvent can result in the formation of disulfides. Additionally, disulfide formation has been observed if the reaction is not performed in an inert, oxygen-free atmosphere.

Figure 2:
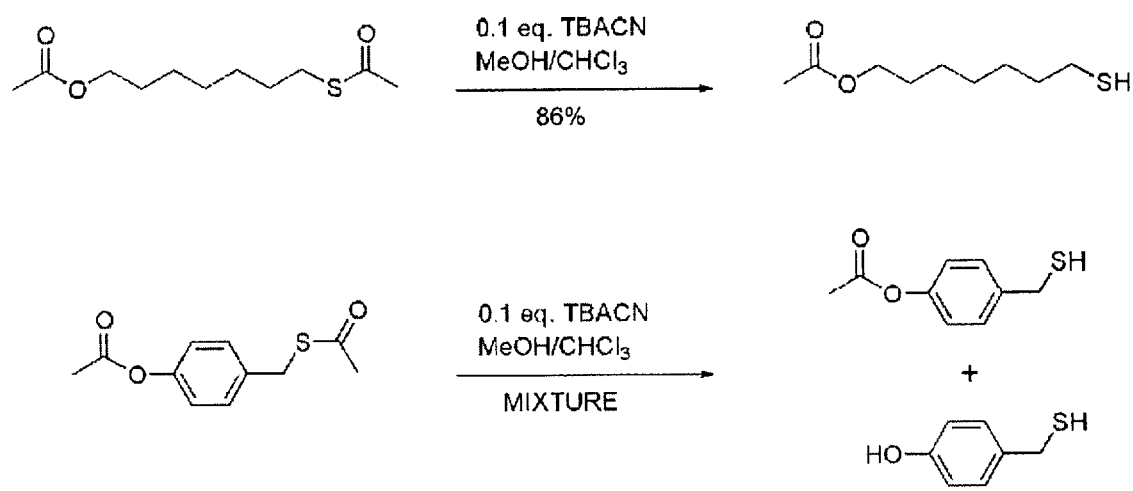
FIG. 2 shows selective deprotection of difunctional thioacetates.

A protic solvent is used in this method. Reactions incorporating methanol may result in higher yields and absence of side product formation in comparison to ethanol and halogen-substituted alcohols. Acidic solvents ($pK_a$<15) or certain functional groups such as amines, haloaliphatics, and fluoroaromatics may hinder the catalytic process. In difunctional aliphatic systems that include thioacetate and acetate functional groups, it has been observed that the cyanide may chemoselectively deprotect the thioacetate, maintaining the unhindered acetate (FIG. 2).

The efficiency of the method may be denoted by the amount of quaternary ammonium cyanide or tetrabutylammonium cyanide required for conversion of the thioacetate to the free thiol. Standard literature procedures employ an excess (>1 mol equiv) of the deprotecting agent per thioacetate group, whereas catalytic amounts of tetrabutylammonium cyanide can sufficiently convert the thioacetate to the free thiol product, ultimately lowering the quantity of material needed for each reaction. Several experiments implemented a variety of reaction times and TBACN quantities (0.1–0.7 mol equiv) to determine the effective limits of the catalytic process. Longer reaction times (≦5 h) may required for catalytic amounts lower than 0.5 equiv and for greater than 60% conversion to the free thiol. Higher amounts of catalyst may fully convert the thioacetates to the free thiol in a shorter amount of time (<3 h), but may result in a higher tendency for side products to form.

The thioester compound, $R^1$—S—CO—$R^2$, in which the process of this invention converts it to a thiol compound, $R^1$—SH, has many structural variations and some restrictions. The bonding site on the $R^1$ group to sulfur must be a saturated carbon atom. This saturated carbon bonding site may be a primary carbon (—$CH_2$—, compounds 1, 3–10 in example 1), secondary carbon (—CH—) structure or a tertiary carbon (—C—, compound 2 in example 1). Beyond the carbon linkage point in the $R^1$ group a wide variety of hydrocarbon substitutents and heteroatom functional groups may be incorporated. These substituents include but are not limited to: simple and branched alkanes (such as compound 1 in example 1); cycloaliphatic stuctures (such as compound 10 in example 1); arylaliphatic structures (such as benzylic, compound 3 in example 1; phenethyl, compound 4 in example 1; trityl, compound 2 in example 1); alkenes; and alkynes. The heteroatom functional groups include but are not limited to: ethers (such as compound 5 in example 1); thioethers; non-aromatic alcohols; amines; ketones; aldehydes; esters (such as compound 11 in example 1); amides; nitriles; haloaryliphatic structues (such as halobenzylic, compounds 6–9 in example 1); and any other functionality that is not sufficiently acidic in nature to interfere with the thioacetate deprotection mechanism. Polyfunctional thioacetates (such as o-xylyldithiol, compound 13 in example 1) are also readily deprotected. Optionally, the $R^1$ group does not contain acidic functional groups, carboxylic group, thioaromatic, sulfonic acid, phosphonic acid, fluoroalcohol, or an aromatic structure directly bonded to the sulfur atom.

TBACN may not be effective for some aromatic thiol deprotections. The thiophenolate anion may be insufficiently basic to abstract a proton from methanol. More acidic alcohols may not counter this effect. The cyanide ion may be protonated by the more acidic alcohols so that the initial reaction does not occur. (It should be noted that the reactivity of cyanide salts with acids to generate HCN gas can be potentially dangerous and fatal if improperly supervised or inhaled.)

Having described the invention, the following examples are given to illustrate specific applications of the invention. These specific examples are not intended to limit the scope of the invention described in this application.

Example 1

General synthesis procedure—All synthetic procedures were performed under an inert nitrogen atmosphere with oven dried glassware. Solvents were dried by passage through activated alumina columns and degassed with nitrogen prior to use. All reagents and catalysts were purchased from Aldrich and used as received except for compounds 10 and 11, which were synthesized. (Note: without proper storage in a dry box or dessicator, it has been observed that tetrabutylammonium cyanide can lose effectiveness over time). $^1$H and $^{13}$C NMR were recorded on a Bruker Avance-300 instrument. Chemical shifts are reported in parts per million (ppm) and referenced to the residual chloroform peak at 7.28 and 77.0 ppm, respectively.

Initially a series of both aliphatic and aromatic thiol and thioacetate functionalized compounds (compounds 1–13) were chosen for deprotection studies. The thiols were converted to their respective thioacetates by reaction with acetic anhydride in a pyridine-dichloromethane mixture in high yield. Proton and carbon NMR spectra of reacted thioacetates were compared to the commercial materials and analyzed for side products, conversion and yields.

Example 2

General deprotection procedure for monothioacetates 1–10—Under an atmosphere of nitrogen, tetrabutylammonium cyanide (0.5 mol equiv) was added to chloroform (2 mL), methanol (2 mL), and monothioacetate reagent (0.1 g).

After stirring for 3 h at room temperature under nitrogen, distilled water (10 mL) and chloroform (10 mL) were added, the organic layer was separated, and the aqueous layer was extracted with chloroform (10 mL). The organic layers were combined, washed with ammonium chloride (aq) (10 mL), dried with MgSO$_4$, filtered, and concentrated in vacuo. After purification by column chromatography on silica gel (hexane), the product was obtained and dried in vacuo. The spectral data for 1–9 are analogous to those obtained for a commercial sample. The synthesis, boiling point, and elemental data for compound 10 has previously been reported and was analogous to this product (Sun et al., "Anhydrous Tetrabutylammonium Fluoride" *J. Am. Chem. Soc.*, 127(7), 2050 (2005)).

Cyclohexylethanethiol (10): $^1$H NMR (300 MHz, CDCl$_3$): δ 2.56 (q, 2H, J=6.3 Hz), 1.64–1.73 (m, 5H), 1.53 (q, 2H, J=7.8 Hz), 1.17–1.41 (m, 5H), 0.83–1.0 (m, 2H). $^{13}$C NMR (75 MHz, CDCl$_3$): δ 41.8, 36.5, 32.9, 26.6, 26.2, 22.2.

The aliphatic thiol series included normal alkane, trityl, ethyl-cyclohexyl, phenethyl, phenoxyethyl, benzyl, and p-halobenzyl moieties. With the exception of the p-fluorobenzyl thioacetate, all yields were ≦80%. The effect of the fluorine substitution or even a fluorocarbon presence in the reaction medium is not understood at this time. In the case for compound 9 there was no evidence of ring substitution by the cyanide at the fluorine position.

Example 3

General deprotection procedure for diacetate 11–12— Analogous procedure for reactions 1–10 except 0.1 mol equiv of tetrabutylammonium cyanide was used and the reaction was stirred for 16 h. The synthesis and elemental data for compound 11 has previously been reported and were analogous to this product (Miller et al., "Adsorbed ω-Hydroxy Thiol Monolayers on Gold Electrodes: Evidence for Electron Tunneling to Redox Species in Solution" *J. Phys. Chem.*, 95(2), 877 (1991); Carter et al. "Distance Dependence of the Low-Temperature Electron Transfer Kinetics of (Ferrocenylcarboxy)-Terminated Alkanethiol Monolayers" *J. Am. Chem. Soc.*, 117(10), 2896 (1995). Although a mixture of products was observed for 12, a higher ratio of thioacetate was deprotected than acetate (~65/35).

Mercaptoheptylacetate (11): $^1$H NMR (300 MHz, CDCl$_3$): δ 4.06 (t, 2H, J=6.6 Hz), 2.53 (q, 2H, J=7.2 Hz), 2.06 (s, 3H), 1.56–1.65 (m, 5H), 1.26–1.45 (m, 6H). $^{13}$C NMR (75 MHz, CDCl$_3$): δ 171.2, 64.5, 33.9, 28.7, 28.5, 28.2, 25.8, 24.5, 21.0.

Difunctional α-thiol-ω-alcohol and α-thiol-ω-phenol were acylated to the corresponding acetates (compounds 11 and 12, respectively) and competitive deprotection reaction undertaken. Compound 11 displayed a sequential cleavage wherein the thioacetate was converted to the thiol prior to any conversion of the acetate.

Example 4

Figure 3:
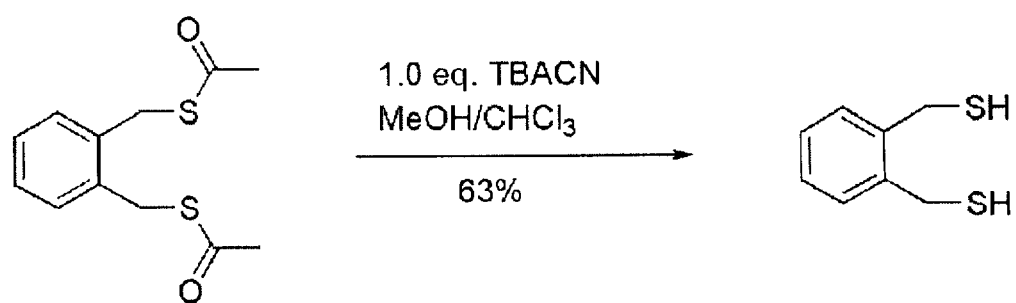
FIG. 3 shows deprotection of dithioacetate.

General deprotection procedure for dithioacetate 13—The bifunctional o-xylylene dithiol (compound 13) was acylated and then deprotected using TBACN (FIG. 3). Analogous procedure for reactions 1–10 except 1.0 mol equiv of tetrabutylammonium cyanide was used and the reaction was stirred for 16 h. The spectral data are analogous to those obtained for a commercial sample. Some side product formation and generally lower yields were revealed than for the monothioacetates. The yield was 63% with some byproduct formation, probably disulfide.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A method comprising:
providing a compound of the formula:

wherein R$^1$ is an organic group in which the bonding to sulfur is through a saturated carbon; and
wherein R$^2$ is an aliphatic group; and
reacting the compound with a quaternary ammonium cyanide salt in the presence of a protic solvent in an inert atmosphere to convert the compound to a product of the formula:

2. The method of claim 1, wherein R$^2$ is methyl.
3. The method of claim 1, wherein the quaternary ammonium cyanide salt is a tetraalkylammonium cyanide.
4. The method of claim 1, wherein the quaternary ammonium cyanide salt is a tetra(C$_1$-C$_4$)ammonium cyanide.
5. The method of claim 1, wherein the quaternary ammonium cyanide salt is tetrabutylammonium cyanide.
6. The method of claim 1, wherein the protic solvent is methanol.
7. The method of claim 1, wherein the reaction is performed in the presence of a nonprotic solvent in which the compound is soluble.
8. The method of claim 7, wherein the nonprotic solvent is chloroform.
9. The method of claim 7, wherein the nonprotic solvent is dichloromethane or tetrahydrofuran.
10. The method of claim 1, wherein the stoichiometric ratio of cyanide to sulfur is from about 0.1 to about 0.7.
11. The method of claim 1, wherein the compound is a monothioacetate.
12. The method of claim 1, wherein the compound has more than one thioacetate functional group.
13. The method of claim 1, wherein the compound contains an acetate group that is not removed in the reacting step.
14. The method of claim 1, wherein R$^1$ contains one or more groups selected from non-acidic functional group, alkene, alkyne, non-aromatic alcohol, ether, thioether, amine, ketone, aldehyde, ester, amide, nitrile, and haloaraliphatic with the halogen bonded to the aromatic moiety and sulfur bonded to the aliphatic moiety.
15. The method of claim 1, wherein R$^1$ does not contain acidic functional groups.
16. The method of claim 1, wherein R$^1$ does not contain carboxylic group, thioaromatic, sulfonic acid, phosphonic acid, or fluoroalcohol.
17. The method of claim 1, wherein R$^1$ does not contain an aromatic structure directly bonded to the sulfur atom.
18. The method of claim 1, wherein R$^1$ is alkyl, decyl, araliphatic with sulfur bonded to the aliphatic moiety, triphenylmethyl, benzyl, phenylethyl, araliphatic ether, phenoxyethyl, haloaraliphatic, halobenzyl, aliphatic, cyclohexylmethyl, aliphatic ester, acetylheptyl, araliphatic ester, acetylbenzyl, aliphatic thioester, or 7-thioacetylxyl-8-yl.

* * * * *